United States Patent [19]

Simons, Jr.

[11] 4,296,206

[45] Oct. 20, 1981

[54] IRREVERSIBLE ANTI-GLUCOCORTICOIDS

[75] Inventor: S. Stoney Simons, Jr., Bethesda, Md.

[73] Assignee: United States of America, Washington, D.C.

[21] Appl. No.: 145,350

[22] Filed: Apr. 30, 1980

[51] Int. Cl.³ .............................................. C12N 5/00
[52] U.S. Cl. .................................... 435/240; 424/243
[58] Field of Search ................. 435/240, 948; 424/243

[56] References Cited

PUBLICATIONS

Failla et al., *Proc. Natl. Acad. Sci. USA*, 72(10), 3849–3852 (1975).
Pifferi et al., Chemical Abstracts 90:23407k, 690 (1979).
Gopalakrishnan et al., *J. Biol. Chem.*, 252(8), 2717–2725 (1977).
Simons et al., *Biochemistry*, 18(22), 4915–4922 (1979).
G. B. Cutler, et al., "11-Deoxycortisol; A. Glucocorticoid Antagonist in Vivo", *The Endocrine Society*, 104, No. 6, 1839 (1979).
G. G. Rousseau, et al., "17 B -Carboxamide Steroids are a new class of Glucocorticoid Antagonist", *Nature*, 279, 158–160 (1979).
H. H. Samuels and G. M. Tomkins, Journal of Molecular Biology 52, 57–74 (1970).
G. G. Rousseau, et al., "Glucocorticoid Receptors: Relations between Steriod Binding and Biological Effects", *Journal of Molecular Biology*, 67, 99–115 (1972).

Primary Examiner—Esther M. Kepplinger
Attorney, Agent, or Firm—Holman & Stern

[57] ABSTRACT

The use of cortisol-21-mesylate and dexamethasone-21-mesylate as inhibitors of glucocorticoid steroid hormone action is disclosed. These compounds were found to be irreversible inhibitors of glucocorticoid action, for example, in both whole and broken rat hepatoma tissue culture cells. The compounds contain both the basic glucocorticoid structure and a reactive functional group capable of yielding a covalent receptor-steroid complex.

5 Claims, 6 Drawing Figures

IRREVERSIBLE ANTI-GLUCOCORTICOIDS

BACKGROUND AND SUMMARY OF THE INVENTION

The present invention relates to the use of cortisol-21-mesylate and dexamethasone-21-mesylate as inhibitors of glucocorticoid action. More particularly, the present invention relates to the use of cortisol-21-mesylate and dexamethasone-21-mesylate as irreversible anti-glucocorticoids.

A major obstacle in elucidating the mechanism of glucocorticoid steroid hormone action has been the characterization and purification of the steroid receptor. Steroid-free receptors are labile proteins which are found in very low concentrations in the cytoplasm of responsive cells. The only apparent activity of the free receptor is its ability to bind steroid reversibly. Thus the availability of a stabilized, covalent receptor-steroid complex would greatly facilitate chemical and biochemical studies of the receptor and its steroid binding site. This in turn could lead to applications in non-operable, hyper-glucocorticoid syndromes, in animals and in man.

Very few anti-glucocorticoids containing the basic glucocorticoid-specific steroid structure are known. It has now been found, in accordance with the present invention, that cortisol-21-mesylate (CM) and dexamethasone-21-mesylate, (DM) which contain both the basic glucocorticoid structure and a reactive functional group capable of yielding a covalent receptor-steroid complex, function as irreversible anti-glucocorticoids. For example, these compounds have a low but significant cell-free affinity for the glucocorticoid receptors of rat hepatoma tissue culture (HTC) cells. While occupancy of the glucocorticoid receptors in whole HTC cells is known to correlate with the induction of the enzyme tyrosine aminotransferase (TAT), CM does not induce TAT in HTC cells. DM gives little induction of TAT in HTC cells ($\sim 25\%$ of full induction). However, CM and DM are potent inhibitors of TAT induction by dexamethasone in whole cells; and, the blockage of dexamethasone induction of TAT by pre-incubating HTC cells with CM or DM cannot be reversed by washing the cells. This is in contrast with the ready reversal of the effects of pre-incubating HTC cells with progesterone, which is a known, reversible anti-glucocorticoid with a non-glucocorticoid structure.

The irreversible block of TAT induction by CM or DM in whole cells is not due to cell toxicity, as shown by protein content, cell number and the ability of the cells to exclude trypan blue. In cell-free systems, pre-incubation of steroid-free receptors with CM or DM inhibits the subsequent ability of the bound receptors to exchange-bind added $^3$H-dexamethasone. Together, these results indicate that CM and DM are irreversible inhibitors of glucocorticoid action in whole and broken HTC cells. As such, the glucocorticoid-like CM and DM appear to be the first irreversible anti-glucocorticoids, possibly due to the formation of irreversible, covalent receptor-steroid complexes with these compounds.

The compounds employed in the present invention are $\alpha$-keto-methanesulfonate derivatives of active glucocorticoid steroids. thus, cortisol-21-mesylate or CM is 4-pregnene-11$\beta$, 17$\alpha$, 21-triol-3, 20-dione-21-methane-sulfonate. Dexamethasone-21-mesylate or DM is 16$\alpha$-methyl-9$\alpha$-fluoro-1,4-pregnadiene-11$\beta$, 17$\alpha$, 21-triol-3, 20-dione-21-methane-sulfonate. As described in detail hereinafter, these $\alpha$-keto-mesylates react both in cell-free and whole cell environments, probably with the glucocorticoid receptor itself, to cause a blockage of a normal glucocorticoid induced response, i.e., the induction of the enzyme tyrosine aminotransferase. The amount of CM or DM which is effective to provide activity as an irreversible anti-glucocorticoid is in the range of from about $10^{-9}$ M to about $10^{-5}$ M.

The use of CM or DM as an irreversible anti-glucocorticoid provides for blocking of the action of glucocorticoid steroid hormones. Such blocking action would be important, for example, in the treatment of non-operable hyperglucocorticoid syndromes, such as adrenal carcinomas and ectopic ACTH syndrome, by blocking the action of elevated levels of glucocorticoids. Treatment would also be possible with patients who are hyper-responsive to glucocorticoids, such as patients with open-angle glaucoma or those who are homozygous for the postulated gene defect which causes this disease, by blocking some of the steroids and thus attenuating the responses in sensitive cells. Additional uses would include pre-operative treatment of patients with Cushing's disease in order to block the effects of glucocorticoids and thus eliminate the complications of surgery due to elevated levels of glucocorticoids. A still further use of the present method would be in studies directed to the mechanism of glucocorticoid hormone action.

BRIEF DESCRIPTION OF THE DRAWINGS

The advantages and features of the invention will be more fully understood from the following description of the preferred embodiments, taken in conjunction with the accompanying drawings, wherein.

DESCRIPTION OF THE PREFERRED EMBODIMENTS

Figure 1:
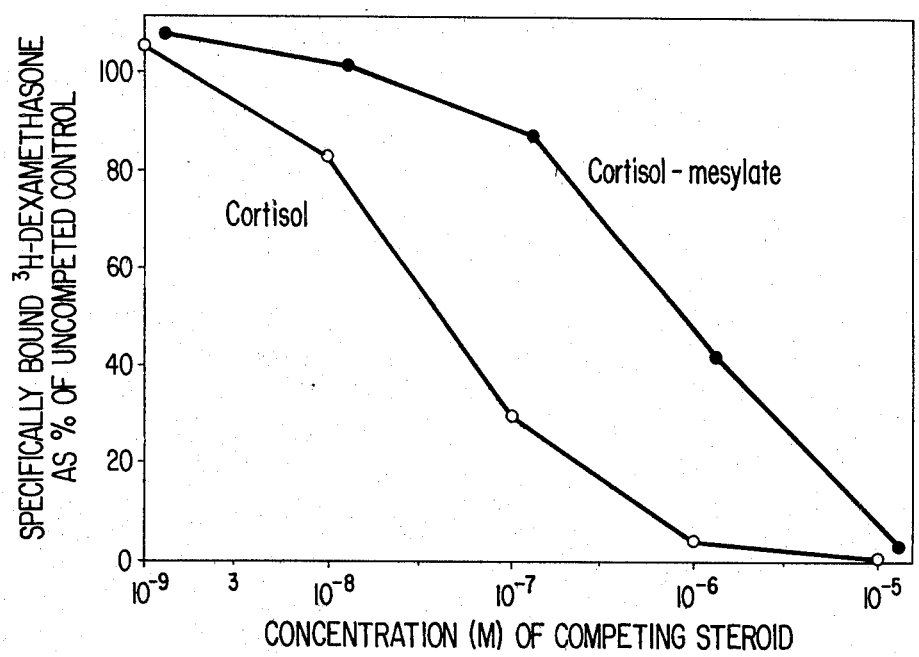
FIGS. 1 through 5 are graphs of various data obtained in the use of cortisol-21-mesylate as an irreversible anti-glucocorticoid, as described hereinafter.

Steroid antagonists have been quite useful in studying the mechanism of steroid hormone action, both in vivo and in vitro. Nafoxidine and tamoxifen have been extensively employed in studies of estrogen action. Investigations with the anti-glucocorticoid progesterone led to the allosteric model of glucocorticoid action. Steroidal antagonists also have been invaluable in treating endocrine-sensitive tumors, e.g., nafoxidine and tamoxifen therapy for breast cancers, and in correcting certain endocrine imbalances, such as spironolactone treatment for hyper-mineralocorticoid syndromes.

The present interest in steroidal antagonists, and specifically anti-glucocorticoids, is primarily for two reasons. First, there are very few anti-glucocorticoids with glucocorticoid-like structures and, so far as is known, none are irreversible. For examples of such previously known structures, Cutler, G. B., Endocrin., 104, 1839–1844 (1979) and Rousseau, G. G. et al., Nature, 279, 158–160 (1979) disclose anti-glucocorticoids with glucocorticoid-like structures. Until just recently anti-glucocorticoids were non-glucocorticoid steriods which are not specific for glucocorticoid receptors and are potent hormones in other endocrine systems, as described, for example, in Rousseau, G. G. et al., J.

Steroid Biochem., 8, 911–919 (1977). One approach to this problem is to look for anti-glucocorticoid activity among derivatives of known glucocorticoids, which should exhibit much less activity in other steroid systems. Second, an irreversible anti-glucocorticoid is a potential affinity label of the steroid binding site of the glucocorticoid receptor. Such a compound would be helpful in isolation and structure studies of the glucocorticoid receptor.

Several chromatographic and immunologic methods of purifying glucocorticoid receptors have recently been advanced, as described, for example, in Failla, D., et al., Proc. Natl. Acad. Sci. USA, 72, 3849–3852 (1975), but affinity labeling has the added advantage that it can be used to probe the steroid binding site. Furthermore, a covalent receptor-steroid complex may impose a block in the normal course of steroid hormone action, which has numerous advantages for mechanistic studies and possible clinical applications. Thus the primary objective was to find a reactive derivative of a known glucocorticoid that is an irreversible anti-glucocorticoid and thus an excellent candidate for a specific, affinity label steroid for glucocorticoid receptors.

The current limited success in affinity labeling steroid receptors and glucocorticoid receptors in particular, as described, for example, in Masry, A. H. et al., J. Med. Chem., 20, 1134–1139 (1977), has prompted the development of new methods of affinity labeling and new affinity label functional groups. In the example below, there is described the cell-free and whole cell properties of a derivative of the glucocorticoid cortisol, containing the reactive α-keto-mesylate group, i.e., cortisol-21-mesylate or CM. The results indicate that CM is an irreversible inhibitor of glucocorticoid action in whole and broken cells. The compound dexamethasone-21-mesylate (DM) has been found to act in a similar manner as an irreversible inhibitor. The DM material has been found to have an approximately 10-fold higher affinity for cell free receptors than CM.

EXAMPLE 1

$^3$H-dexamethasone (24 Ci/mmole) was purchased from Amersham. $^1$H-dexamethasone was a gift from Dr. T. Y. Shen of Merck, Sharp and Dohme. $^1$H-cortisol was purchased from Sigma. The growth of HTC cells in spinner or monolayer cultures has been previously described in Samuels, H. H. et al., J. Mol. Biol., 52, 57–74 (1970) and Gopalakrishnan, T. V., et al., J. Biol. Chem., 252, 2717–2725 (1977) which are incorporated herein by reference. The spinner culture cells were centrifuged in a 0° rotor (700 xg/15 min), washed twice with PBS (700 xg/0°/5 min) and stored at −20° C. for up to 3 months before being used. Unless otherwise specified, the temperature of the whole cell assays was 37° while the cell-free assays were conducted at 0°–4°. Details of the cell-free competition assay and the whole cell biological assays with monolayer cultures are described in Simons, S. S., et al., Biochem. Biophys. Res. Comm, 86, 793–800 (1979) which is incorporated herein by reference. The cell-free exchange assay was carried out by a method in which typically 1.28 ml of HTC cell cytosol was added to 21 μl of $1.0 \times 10^{-5}$ M cortisol in 2.22 ml of homogenization buffer and incubated for 3 h at 0° C. Charcoal (0.425 ml of 10% wt/vol of dextran coated activated charcoal in homogenization buffer) was added to remove the free steroid. After 5 sec. of vortexing, the solution was centrifuged (5000 g/10 min/0° C.) and the supernatant was divided. To one part, [$^3$H]-dexamethasone was added to give a final concentration of $1.9 \times 10^{-8}$ M; to the other, [$^1$H]-dexamethasone was added to a final concentration of $1.1 \times 10^{-5}$ M before introducing [$^3$H]-dexamethasone (final concentration = $1.9 \times 10^{-8}$ M). Duplicate aliquots (235 μl) of each treated portion were worked up at varying times using the method of cell-free competition assay. The total amount of receptor that remained at the end of the exchange assay was estimated from a control solution labelled for 3 h at 0° C. with $7.5 \times 10^{-9}$ M [$^3$H]-dexamethasone ($\pm 4.5 \times 10^{-6}$ M [$^1$H]-dexamethasone) and then treated exactly as for the above solution initially incubated with cortisol. Quantitation of protein and TAT activity was achieved by the methods of Lowry O. H. et al., J. Biol. Chem., 193, 265–275 (1951) and Gopalakrishnan T. V. et al., J. Biol. Chem., 252, 2717–2725 (1977), both of which are incorporated herein by reference. CM was prepared by a method as follows: Methanesulfonyl chloride (1.2 ml, 15.5 mmoles, Aldrich) in 20 ml of tetrahydrofuran (THF) was added dropwise to a stirred solution of 5.0 g of cortisol (13.8 mmol, Sigma) and 2.1 ml triethylamine (15.4 mmol. Aldrich) in 180 ml THF under nitrogen which was maintained at 0° C. for 15 min and then warmed to room temperature. Three hours later, an additional 1 ml of triethylamine (7.2 mmol) and 0.54 ml methanesulfonyl chloride (7.0 mmol) were added. After stirring overnight, the mixture was filtered, concentrated to 25 ml and added to 300 ml H$_2$O. The precipitated solid (5.85 g dec. 158°–159° C.) was dissolved in acetone, filtered, precipitated with petroleum ether and recrystallized from ethyl acetate (yield = 65%, dec. 167°–168° C.). A second crop from ethyl acetate gave 1.03 g (dec. 164°–165° C.). The temperature of decomposition was found to be highly dependent on the rate of heating, even with analytically pure material. Slow rates of heating gave decomposition points that were about 10° lower. After multiple recrystallizations, a final recrystallization from ethyl acetate gave the analytical sample (dec. 179°–181° C.). Ir (nujol) ~3400. 1733, 1659, 1359, 1170 cm$^{-1}$. EI mode mass spectrum gave peaks at m/e (rel. intensities) 440 (P.<<1), 422 (P-H$_2$O, 3), 344 (3), 285 (15), 265 (65), 79 (100), UV (95% EtOH) 242 nm, $\epsilon = 1.68 \times 10^{-4}$ Anal. Calcd. for C$_{22}$H$_{32}$O$_7$S (mol. wt 440.56): C. 59.98; H. 7.32; S. 7.28. Found: C, 60.06, H, 7.46; S. 7.01.

In the event that dexamethasone-21-mesylate (DM) is employed rather than CM, the DM material may be prepared as follows: To 105 mg of dexamethasone (0.268 mmoles) in 2 ml of anhydrous pyridine at 0° was added 25 μl of methanesulfonyl chloride (0.322 mmoles, 1.2 equiv.) with stirring. After 1 hr at 0°, another 0.8 equiv. of methanesulfonyl chloride was added. After a total reaction time of 5 hrs at 0°, the solution was added to 40 ml of ice-water. Filtration, washing with a total of 40 ml of 0° water, drying in a desiccator, and finally drying under high vacuum, afforded a 91% yield of the crude mesylate (m.p. 230°–231° [dec.]) contaminated only by the 21-chloride, as determined by TLC (1:2 benzene: EtOAc on silica gel GF). Two recrystallizations from tetrahydrofuran (THF) gave the analytically pure solid as a solvate, i.e., dexamethasone-21-mesylate-THF (m.p. 231.0°–232.0° [dec.]). Ir (nujol) 3367, 1733 and 1662, 1364 and 1172 cm$^{-1}$; UV (95% EtOH)λ=239 nm ($\epsilon = 1.67 \times 10^4$). Low temperature EI mass spectrum gave a large peak for tetrahydrofuran at m/e=72. Anal. calcd for C$_{23}$H$_{31}$SFO$_7$-THF (mol. wt. 542.65): c, 59.76; H, 7.24; F, 3.50. Found: C, 59.53; H, 7.52; F, 3.78.

RESULTS

In general, the introduction of bulky substituents on the $C_{21}$ of glucocorticoids results in derivatives with a reduced affinity for glucocorticoid receptors as described, for example, in Failla, D. et al., Proc. Nat. Acad. Sci. USA, 72, 3849-3852 (1975). Thus it was not surprising that the affinity of CM for glucocorticoid receptors was found to be 15-fold lower than that of the parent steroid cortisol in a cell-free competition assay using crude receptors from a well characterized line of rat hepatoma tissue culture (HTC) cells, as shown in FIG. 1. The data for FIG. 1 was obtained from a determination of relative affinities of cortisol and cortisol-21-mesylate for HTC cell glucocorticoid receptors in a cell-free competition assay. Duplicate crude HTC cell receptor solutions were incubated for 3 hrs at 0° with $5.6 \times 10^{-9}$ M $^3$H-dexamethasone and varying concentrations of cortisol, or CM (final protein concentration=5.1 mg/ml). A 500 fold excess of $^1$H-dexamethasone was used to determine the level of non-specific binding of $^3$H-steroid. The average specifically bound $^3$H-dexamethasone in the presence of varying concentrations of cortisol or CM was plotted as % of the uncompeted control (variation less than ±4%).

Figure 2:
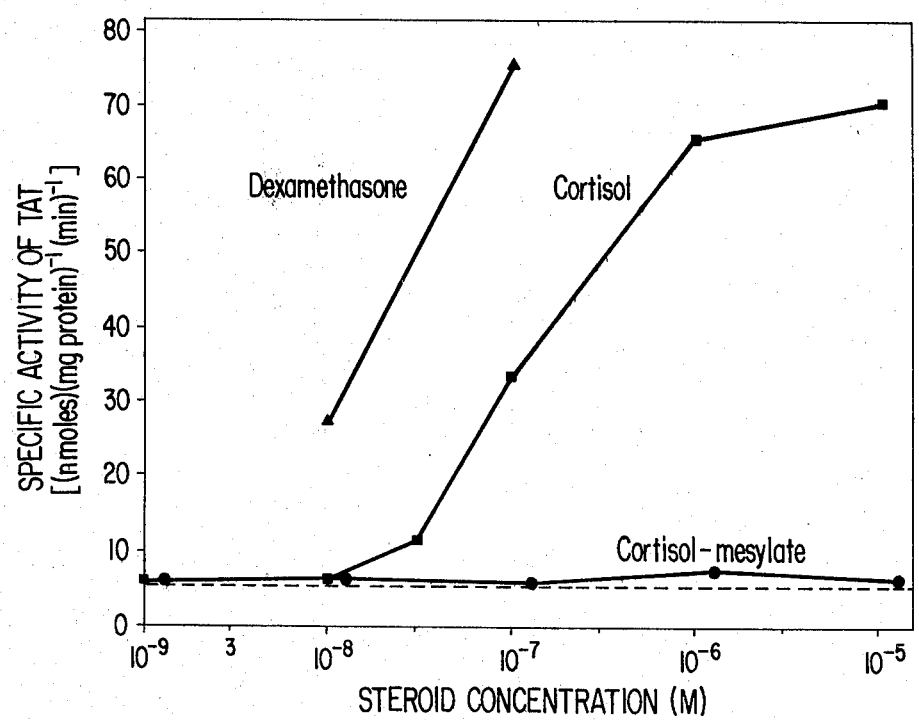

HTC cells display several biological responses to glucocorticoids. Tyrosine aminotransferase (TAT) is one specific, glucocorticoid inducible enzyme in HTC cells; and previous extensive studies argue that TAT induction in HTC cells is a primary response to glucocorticoids that is initiated by the binding of steroid to a specific, cytoplasmic receptor. Since the whole cell dose-induction curve usually agrees quite well with the cell-free binding of all steroid agonists to receptors, it is noteworthy that the whole HTC cell biological activity of CM did not parallel the above determined cell-free affinity of CM for HTC cell receptors. Instead of being 1/15th as active as cortisol in inducing TAT in whole HTC cells, CM was completely inactive. This is shown in FIG. 2 which provides a comparison of the biological activity of dexamethasone, cortisol and cortisol-mesylate in whole HTC cells. Duplicate monolayer cultures of HTC cells were treated with fresh medium containing 1% EtOH±dexamethasone, cortisol or CM for 18 hrs at 37° followed by harvesting and determination of the specific enzyme activity of TAT as previously described. The basal level of TAT activity is shown by the dashed line.

Figure 3:
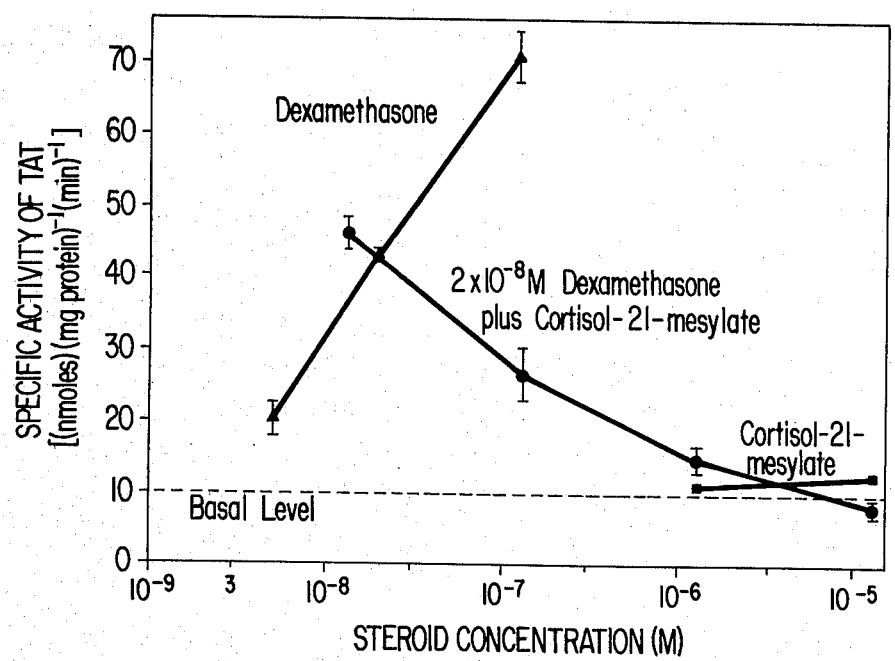

One explanation for this lack of biological activity is that the reactive CM is converted to an inactive steroid. Alternatively, CM could be a anti-inducer, or inhibitor of glucocorticoid action. The inhibition by CM of TAT induction by the glucocorticoid dexamethasone in whole cells as shown in FIG. 3, indicates that the second interpretation is correct, i.e., that CM is an anti-glucocorticoid. The data in FIG. 3 was prepared to test the inhibition of dexamethasone induction of TAT activity in whole HTC cells by cortisol-21-mesylate. Duplicate monolayer plates of HTC cells were treated with medium containing 1% EtOH±dexamethasone or CM as controls and $2 \times 10^{-8}$ M dexamethasone+CM. After the usual incubation (18 hrs/37°) and work-up, the specific enzyme activity of TAT was plotted against the concentration of that steroid present in varying amounts. The range of each duplicate determination is shown by error bars when it exceeds the area of the data points. The basal level of TAT activity is indicated by the dashed line.

The observed inhibition of TAT induction by dexamethasone does not seem to be due to general toxicity of CM for several reasons.

1. In six experiments, the effect of $1.3 \times 10^{-5}$ M CM, for 16 to 18 hrs, on total HTC cell protein content was minor (average of 12% lower than vehicle, cortisol or dexamethasone treated controls). In three experiments involving longer exposure to CM, i.e., 16 hr. pre-incubation with vehicle or $3-6 \times 10^{-6}$ M CM followed by another 24 hrs with added dexamethasone, the proteins in the cells chronically treated with CM were an average of 20% lower than those of the vehicle±dexamethasone controls.

2. In two similar experiments, a comparison of $1.3 \times 10^{-5}$ M CM+$10^{-7}$ M cortisol or $6 \times 10^{-6}$ M CM+$4 \times 10^{-8}$ M dexamethasone vs. vehicle, cortisol or dexamethasone treated controls after 16-24 hrs revealed no effect on cell number and only minor effects on total cell protein (~1% increase to 6% decrease) and cell viability (93-94% vs. 93-97% for controls, as determined by exclusion of trypan blue).

3. While $10^{-7}$ M cortisol in the presence of $1.3 \times 10^{-6}$ M CM was unable to induce TAT, the inductive capacity of the cells remained since, in other experiments $2 \times 10^{-8}$ M of the more potent glucocorticoid dexamethasone in the presence of $1.3 \times 10^{-6}$ M CM did cause a slight but significant increase in TAT as shown in FIG. 3.

4. After about 24 hr, CM was no longer completely inhibitory and some inducibility of TAT return to HTC cells, as described hereinafter.

Figure 4:
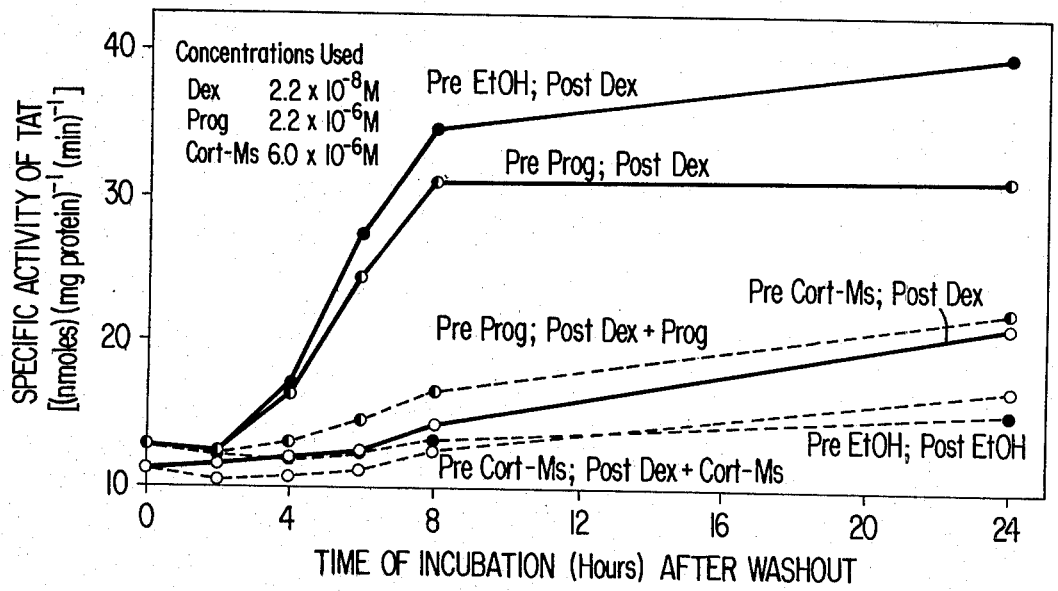

Further analysis of the data of FIG. 3 allows a rough calculation of $K_I$ for CM($\delta 10^{-7}$ M), which is an order of magnitude lower than that expected from the apparent affinity of CM for HTC cell receptors (see FIG. 1). This fact suggests that CM is acting as an irreversible inhibitor of glucocorticoid action. One approach to establishing CM as an irreversible inhibitor of TAT induction by glucocorticoids is to determine whether the effects of CM can be reversed by washing the cells. Thus HTC cells were pre-incubated overnight with vehicle, progesterone (a known reversible anti-glucocorticoid) or CM. The cells were then washed once and resuspended in fresh medium containing $2 \times 10^{-8}$ M dexamethasone±the steroid of pre-incubation. A plot of the ensuing time course of TAT induction in FIG. 4 shows the normal induction of TAT for vehicle, or progesterone, pre-treated cells, thus confirming the reversible nature of progesterone action and the efficacy of the present procedures in removing non-covalently bound steroid. In marked contrast, however, these washing conditions can not reverse the effects of the CM pre-incubation. There is no induction of TAT in the pre-CM, post-dexamethasone treated cells until ~8 hrs, after the wash procedure, a time when the vehicle and progesterone pre-treated cells show almost full induction of TAT.

The data in FIG. 4 were obtained in connection with TAT induction after EtOH, progesterone or cortisol-21-mesylate pre-treatment of HTC cells. Spinner cultures containing 200 ml of HTC cells at $2 \times 10^5$/ml were treated with 0.938 ml of EtOH±$4.69 \times 10^{-4}$ M progesterone or $1.28 \times 10^{-3}$ M CM. After incubation at 37°/15 ½ hrs, ~$6 \times 10^7$ cells were centrifuged at 600 xg/10 min/22° and resuspended in 200 ml of "conditioned" medium that had also been "incubated" at 37°/15 ½ hrs. After a second centrifugation, each cell pellet was again resuspended in 210 ml of "conditioned" medium. Duplicate aliquots (3 ml) were removed for 0 time protein and TAT determinations; and duplicate 50 ml aliquots were placed in 125 ml Wheaton bottles containing 300 μl of EtOH±3.67×10$^{-6}$ M dexamethasone for EtOH pre-incubated cells and 300 μl of EtOH solutions of 3.67×10$^{-6}$ M dexamethasone±3.67×10$^{-4}$ M progesterone (for the progesterone pre-treated cells) or ±1.0×10$^{-3}$ M CM (for the CM pre-treated cells). The cells in Wheaton bottles were incubated in a rotating water bath (37°/175 rpm) with 3 ml aliquots being removed at various time points for protein and TAT determinations in the usual manner. The specific enzyme activity of TAT was then plotted against the length of incubation after the addition of steroid to washed cells for EtOH pre-treated cells treated post-wash out with dexamethasone or EtOH; for progesterone pre-treated cells treated post-wash out with dexamethasone or dexamethasone+progesterone and for CM pre-treated cells treated post-wash out with dexamethasone or dexamethasone+CM. Average variation among duplicates was ±2.4%.

Even 24 hrs after the wash procedure, the magnitude of TAT induction in the pre-CM, post-dexamethasone treated cells is significantly reduced; and, this limited induction can be blocked if CM is added back with dexamethasone after the wash procedure. Finally, it is noteworthy that CM, 24 hrs. after being "removed" from the cells by the washing procedure, is just as efficient in reducing the magnitude of TAT induction as is progesterone when it is continuously present in the cells, as shown in FIG. 4.

Figure 5:
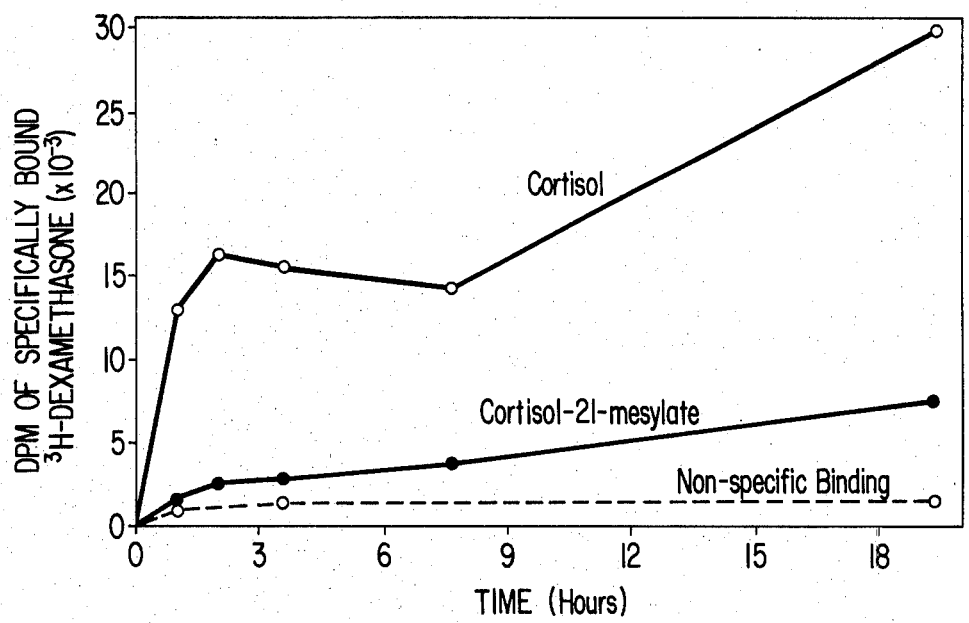

In CM pre-treated cells, the delay of TAT induction by glucocorticoids, as shown in FIG. 4, is consistent with an irreversible reaction between CM and HTC cell receptors to give blocked, covalently labeled receptor-steroid complexes. To examine this possibility in more detail, a determination was made as to whether the cell-free binding of CM to HTC cell receptors is reversible. Using the previously described exchange assay, crude HTC cell receptors were incubated with enough cortisol, or CM, to occupy ~75% of the receptor based on data of FIG. 1. After ~3 hrs, activated charcoal was added to remove free steroid and to inactivate steroid-free receptors. An excess of $^3$H-dexamethasone was then added to exchange-bind to the previously formed receptor-steroid complexes. The data of FIG. 5 show that CM preincubation of HTC cell receptors reduced by ~75% the ability of these receptors to exchange-bind $^3$H-dexamethasone. Thus CM is an irreversible inhibitor of one aspect of glucocorticoid action in broken cells, i.e., the ability of glucocorticoids to exchange-bind to receptor-glucocorticoid complexes.

FIG. 5 is based on data obtained in studying inhibition of $^3$H-dexamethasone exchange binding to preformed complexes by cortisol-21-mesylate. Using the previously described exchange assay, crude HTC cell receptors were pre-incubated with 6×10$^{-8}$ M cortisol or 1.35×10$^{-6}$ M CM for 2.8 hrs at 0° (final protein concentration=7.0 mg/ml). After addition of activated charcoal to remove free steroid, and to inactivate steroid-free receptors, followed by centrifugation to pellet the activated charcoal, the pre-incubated cytosols were adjusted to 1.9×10$^{-8}$ M $^3$H-dexamethasone ±1.1×10$^{-5}$ M $^1$H-dexamethasone. After subsequent incubation for the indicated time, activated charcoal was again added to determine the amount of specifically bound $^3$H-dexamethasone (=total−non-specific binding) that was formed by exchange binding in cortisol or CM pre-incubated cytosols. For comparison, the amount of non-specific binding in cortisol or CM pre-incubated receptor solutions is shown in dashed lines.

DISCUSSION

In accordance with the present invention, a derivative of cortisol has been employed in an effort to obtain an anti-glucocorticoid that is specific for the glucocorticoid receptor and does not exhibit any other steroid hormone activity. In order to increase the possible anti-glucocorticoid activity, and to obtain a potential steroid affinity label, a chemically reactive cortisol derivative was employed. It was postulated that a covalent receptor-steroid complex might be unable to perform the necessary functions leading to increased transcription of a specific gene. Using the thiol specific, α-keto mesylate group, there was prepared cortisol-21-mesylate (CM). This steroid is an inhibitor of glucocorticoid action in a whole cell biological assay, as shown in FIG. 3. As such, CM is one of a small number of anti-glucocorticoids containing glucocorticoid specific structures. Furthermore, the data of FIGS. 4 and 5 indicate that CM is an irreversible anti-glucocorticoid in whole cell and broken cell systems. The apparent $K_I$ of CM is ~1×10$^{-7}$M, which is equal to the $K_d$ of cortisol induction of TAT in HTC cells. However, this $K_I$ for the CM has no physical meaning since an irreversible reaction can not have an equilibrium $K_I$. Numerous rates go into determining the apparent $K_I$ but the rate of decomposition of CM does not appear to be a factor. Several experiments indicate that CM is active as an anti-glucocorticoid in HTC cell cultures for ~18 hrs at 37°. Thus CM is a potent, long lasting anti-glucocorticoid.

While there are a few apparent exceptions, the concentration of a given steroid required to give half-maximal biological response (=$K_d$Bio) is greater than or equal to the $K_d$ of the binding of the same steroid to its receptor. In contrast, the apparent $K_I$ of CM (see FIG. 3) is in order of magnitude less than the apparent $K_d$ of CM for HTC cell glucocorticoid receptors (see FIG. 1). This disagreement is almost certainly due to non-equilibrium conditions with CM, especially in the cell-free competition assay of FIG. 1. While short time competition assays with the tritiated forms of potent glucocorticoids such as dexamethasone are routinely used, a $T_{1/2}$≃100 hrs for the dissociation of dexamethasone from the receptor precludes a true equilibrium measurement. Instead, these competition assays reflect, to a large extent, the varying association rates of steroid and receptor. Since 3 hrs at 0° is enough to inhibit ~75% of the expected exchange-binding of $^3$H-dexamethasone with CM-receptor complexes (see FIG. 5), the above inequality of $K_I$≠$K_d$ can be explained by Equation 1, where $k_2$>>$k_{-1}$ for CM and $k_{-1}$<<$k_1$ for dexamethasone.

Equation 1

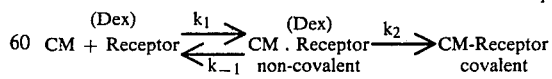

Thus $k_1$ for CM and dexamethasone would be rate limiting in the cell-free competition assay. Only in the much longer whole cell assay at 37° would the binding of dexamethasone be close to true equilibrium, in which case the irreversible formation of covalent CM-Receptor would significantly displace the equilibrium with dexamethasone to cause the apparent low $K_I$ of CM. In this respect, it is also of interest to compare CM with progesterone, a known, reversible anti-glucocorticoid. The apparent $K_d$'s of these steroids with HTC cell glucocorticoid receptors are 15 and 5 times greater, respectively, that the $K_d$ of cortisol, as shown in Rousseau, G. G. et al., J. Steroid Biochem., 8, 911–919 (1977). Thus, all other things being equal, a 3× concentration of CM would be equivalent to a 1× concentration of progesterone. However, due to the irreversible nature of CM, FIG. 4 shows that, over a 24 hr period, a pre-incubation of a 3× concentration of CM followed by washing the cells to remove the free CM causes just as much anti-glucocorticoid activity as does a 1× concentration of progesterone that is continuously present.

The observation that CM is an irreversible anti-glucocorticoid in whole cells would not have been possible if any of the following three conditions did not exist. First, CM has to be reactive and stable, and must have high affinity for the receptor, in order to give some reaction with the receptor (or components that are mandatory for receptor activity) but not be consumed by reacting at 37° with the large excess of other compounds that are present in HTC cells and tissue culture medium. An attempt was made to meet this seemingly impossible specification with the newly described β-hydroxy-α-keto mesylate functional group of CM which specifically and rapidly reacts with thiolate anions ($R\text{-}S^{\ominus}$) but is essentially inert toward other nucleophiles such as thiols, carboxylates, imidazoles, amines and alcohols. Even so, it was pleasantly surprising when the kinetics of TAT inhibition in dexamethasone-CM solutions and of experiments of the type of FIG. 4 indicated that CM was fully active as an irreversible anti-glucocorticoid in tissue culture for 17–18 hrs. This apparent stability suggests possible uses in whole animals.

The second necessary condition is that the glucocorticoid derivative CM should somehow be able to block the action of normal receptor-glucocorticoid complexes. In fact, CM does block the normal action of glucocorticoids (see FIG. 3); but as yet, there is no direct evidence that CM does so by a direct interaction with the receptor, for example by formation of a blocked covalent receptor-steroid complex. Presently it is postulated that non-glucocorticoid anti-glucocorticoids function by binding to that form of the glucocorticoid receptor that does not bind active glucocorticoids. Since CM possesses a basic glucocorticoid structure, it is not clear whether CM would function as above or bind to the same form of receptor that binds active glucocorticoids but cause a block at a later step, such as activation or transformation, by virtue of the covalent steroid-receptor bond which inhibits a necessary reaction or conformational change.

The third necessary condition is that receptor replenishment be slow. If inactivated receptors, or the inactivated factors needed for receptor activity, were rapidly resynthesized as soon as they were inactivated by CM, it would be very difficult to observe any irreversibility on the part of CM. However, this is obviously not the case since removing free CM from pre-treated cells and then adding dexamethasone causes no induction of any TAT for 6–8 hrs. and only partial induction of TAT after 24 hrs. In three experiments, the appearance of TAT in CM pre-treated cells was an average of 2.7 hrs after TAT induction in EtOH or progesterone pre-treated cells. Thus it would appear that the rate of synthesis of new receptors, or receptor factors, is relatively slow.

Figure 6:
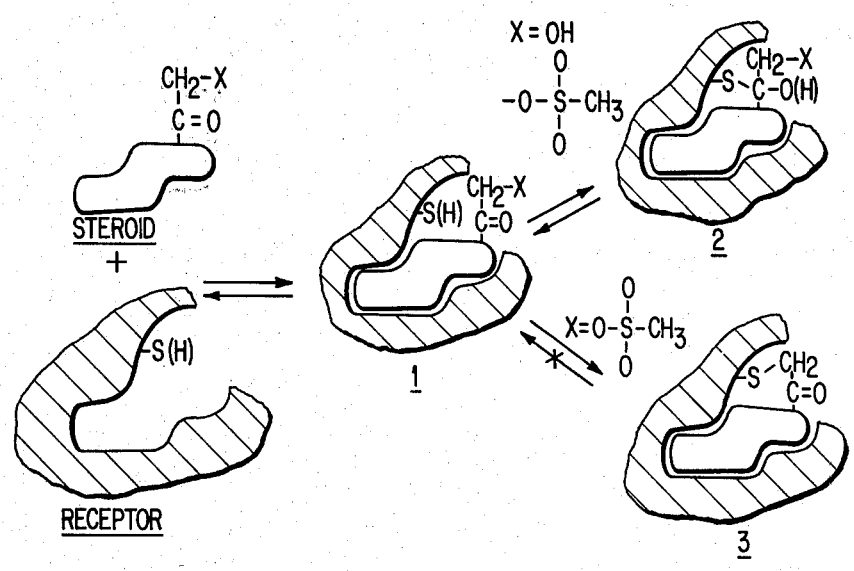
FIG. 6 is a schematic representation of glucocorticoid binding to receptors.

FIG. 6 is a schematic representation of glucocorticoid binding to receptors. All high affinity steroids would give a non-covalent complex 1 which may be equilibrium with the covalent receptor-steroid hemi-thiolketal 2. The non-covalent complex with CM can also react with the receptor to give the irreversible covalent receptor-steroid β-keto thiol ether 3.

In general, all glucocorticoid steroids possess the basic 4-pregnen-11β-ol-3,20-dione structure. Other functional groups are required to give more active glucocorticoids such as cortisol, methylprednisolone, dexamethasone, fluocinolone and triamcinolone. Since cortisol and dexamethasone are representative compounds of the general class of potent glucocorticoids and since cortisol-21-mesylate and dexamethasone-21-mesylate have been found to be irreversible anti-glucocorticoids, it is believed that the $C_{21}$-mesylates of other yet untested (and some yet unsynthesized) potent glucocorticoids will also be effective irreversible anti-glucocorticoids. In fact, the $C_{21}$-mesylates of glucocorticoids more active than dexamethasone should be effective at doses lower than those used for CM and DM (i.e., $10^{-9}$ M – $10^{-5}$ M) and thus may be less toxic to animals and man.

In the experiments and uses of CM and DM described above, the toxicity of either compound was negligible. In one experiment with rats, some anti-glucocorticoid activity by CM was observed with daily, intraperitoneal injections of 10–50 mg CM per kilogram of rat body weight. When higher doses (i.e., $\geq 100$ mg/kilogram) were used to increase the anti-glucocorticoid effects, peritonitis and death of the animal resulted. From these data, it is likely that doses of 2–15 mg CM/kilogram would be active, but not lethal, in man. In order to be more useful in animals and people, two approaches can be used to reduce this toxicity. First, use more potent irreversible anti-glucocorticoids, such as DM and the $C_{21}$-mesylates of other more potent glucocorticoids (e.g., fluocinolone and triamcinolone). Second, alternative routes of administration (e.g., oral, intravenous, intramuscular and subcutaneous) might be less toxic.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely preferred embodiments thereof.

The embodiments of the invention in which exclusive property or privilege is claimed are defined as follows:

1. In a method for inhibiting glucocorticoid action, the improvement which comprises the use as the inhibitor of a compound selected from the group consisting of cortisol-21-mesylate and dexamethasone-21-mesylate.

2. The method of claim 1 wherein the inhibitor is cortisol-21-mesylate.

3. The method of claim 2 wherein cortisol-21-mesylate is employed in inhibiting tyrosine aminotransferase induction in hepatoma tissue culture cells.

4. The method of claim 1 wherein the inhibitor is dexamethasone-21-mesylate.

5. The method of claim 4 wherein dexamethasone-21-mesylate is employed in inhibiting tyrosine aminotransferase induction in hepatoma tissue culture cells.

* * * * *